(12) United States Patent
Hell et al.

(10) Patent No.: US 8,174,692 B2
(45) Date of Patent: *May 8, 2012

(54) HIGH SPATIAL RESOLUTION IMAGING OF A STRUCTURE OF INTEREST IN A SPECIMEN

(75) Inventors: Stefan W. Hell, Göttingen (DE); Jonas Fölling, Heidelberg (DE); Christian Eggeling, Göttingen (DE); Alexander Egner, Einbeck (DE); Andreas Schönle, Göttingen (DE); Mariano Bossi, Buenos Aires (AR)

(73) Assignee: Max-Planck-Gesellschaft zur Foerderung der Wissenschaften e.V., Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/949,159

(22) Filed: Nov. 18, 2010

(65) Prior Publication Data

US 2011/0081653 A1      Apr. 7, 2011

Related U.S. Application Data

(63) Continuation of application No. PCT/EP2009/056194, filed on May 20, 2009.

(30) Foreign Application Priority Data

May 21, 2008   (DE) .......................... 10 2008 024 568
Sep. 15, 2008   (EP) ...................................... 08164352

(51) Int. Cl.
    *G01J 3/30*      (2006.01)
(52) U.S. Cl. ........................................................ 356/317

(58) Field of Classification Search .......... 356/317–318, 356/417
See application file for complete search history.

(56) References Cited

U.S. PATENT DOCUMENTS 6,667,830 B1    12/2003  Iketaki
7,880,150 B2 *   2/2011  Hell et al. ................. 250/459.1
(Continued)

FOREIGN PATENT DOCUMENTS

DE    10 2006 021 317 B3    10/2007
(Continued)

OTHER PUBLICATIONS

Rust et al., "Sub-diffraction-limit imaging by stochastic optical reconstruction microscopy (STORM) in Nature Methods," vol. 3, 2006, p. 793-796.

(Continued)

*Primary Examiner* — Kara E Geisel
(74) *Attorney, Agent, or Firm* — Thomas, Kayden, Horstemeyer & Risley, LLP

(57) ABSTRACT

In high spatial resolution imaging, a structure in a specimen is marked with a substance which, in a first electronic state, is excited by light of one wavelength to emit fluorescent light, which is also converted from its first into a second electronic state by that light, and which returns from its second into its first electronic state. The specimen is imaged onto a sensor at a spatial resolution not resolving an average spacing between neighboring molecules of the substance, and exposed to the light at such an intensity that the molecules in the first state are alternately excited to emit fluorescent light and converted into their second state, and that at least 10% of the molecules presently in their first state lie at a distance from their closest neighboring molecules in their first state which is greater than the spatial resolution of the imaging onto the sensor.

20 Claims, 4 Drawing Sheets

U.S. PATENT DOCUMENTS

| | | | |
|---|---|---|---|
| 2001/0045529 A1* | 11/2001 | Iketaki et al. | 250/493.1 |
| 2004/0212799 A1 | 10/2004 | Hell | |
| 2006/0038993 A1 | 2/2006 | Hell | |
| 2008/0032414 A1 | 2/2008 | Zhuang et al. | |
| 2008/0076142 A1 | 3/2008 | Knebel et al. | |
| 2008/0088839 A1* | 4/2008 | Hell et al. | 356/318 |
| 2009/0134342 A1 | 5/2009 | Hell et al. | |
| 2009/0206251 A1* | 8/2009 | Hess et al. | 250/459.1 |
| 2009/0279086 A1 | 11/2009 | Hell | |
| 2010/0181535 A1 | 7/2010 | Tinnefeld et al. | |
| 2011/0160083 A1* | 6/2011 | Hell et al. | 506/12 |

FOREIGN PATENT DOCUMENTS

| | | |
|---|---|---|
| EP | 1 903 336 A1 | 3/2008 |
| WO | 2006/127692 A2 | 11/2006 |
| WO | WO 2006/133944 * | 12/2006 |
| WO | 2007/030835 A2 | 3/2007 |
| WO | 2008/074429 A1 | 6/2008 |
| WO | 2008/080032 A2 | 7/2008 |
| WO | 2009/003948 A2 | 1/2009 |

OTHER PUBLICATIONS

C. Geisler, A. Schönle, C. von Middendorff, H. Bock, C. Eggeling, A. Egner and S. W. Hell, "Resolution of −/10n fluorescence microscopy using fast single molecule photo-switching," Appl. Phys. A 88, 223-226 (2007).

S. Bretschneider et al., "Breaking the diffraction barrier in fluorescence microscopy by optical shelving," Phys. Rev. Lett. 98, 218103 (2007).

Falling, J.; Bossi, M.; Bock, H. et al., "Fluorescence nanoscopy by ground-state depletion and single-molecule return", Nat. Meth. vol. 5, No. 11, Nov. 2008, p. 943-945.

Heilemann, Conventional Fluorescent M.; van de Linde S.; Schüttpelz, M. et al., "Subdiffraction-Resolution Fluorescence Imaging with Conventional Fluorescent Probes," Angew. Chem. Int. Ed., vol. 47, 2008, p. 6172-6176.

van de Linde, S.; Schüttpelz, M.; Kasper, R. et al., "Photoswitching microscopy with subdiffraction-resolution," Proc. of SPIE: Single Molecule Spectroscopy and Imaging II. edited by J. Enderlein et al., vol. 7185, 2009, p. 71850E-1 through -11.

Betzig, E.; Patterson , G. H.; Sougrat, R. et al., "Imaging Intracellular Fluorescent Proteins at Nanometer Resolution," Science, vol. 313, Sep. 2006, p. 1642-1645.

Lidke, K. A.; Rieger, B.; Jovin, T. M.; Heintzmann, R., "Superresolution by localization of quantum dots using blinking statistics," Opt. Express, vol. 13, No. 18, Sep. 2005, p. 7052-7062.

Bates, M.; Blosser, T. R.; Zhuang, X., "Short-Range Spectroscopic Ruler Based on a Single-Molecule Optical Switch," Phys. Rev. Lett., vol. 94, 2005, p. 108101-1 through -4.

Enninga, J.; Sansonetti, P.; Tournebize, R., "Roundtrip explorations of bacterial infection: from single cells to the entire host and back," TRENDS in Microbiol., vol. 15, No. 11, 2007, p. 483-490.

Gordon, M. P.; Ha, T.; Selvin, P. R., "Single-molecule high-resolution imaging with photobleaching." Proc. Natl. Acad. Sc. vol. 101, No. 17, 2004, p. 6462-6465.

Chudakov, D. M.; Verkhusha, V. V.; Staroverov, D. B. et al., "Photoswitchable cyan fluorescent protein for protein tracking," Nat. Biotechn., vol. 22, No. 11, Nov. 2004, p. 1435-1439.

Hess, S. T.; Girirajan, T. P. K.; Masom, M. D., "Ultra-High Resolution Imaging by Fluorescence Photoactivation Localization Microscopy," Biophys. J., vol. 91, Dec. 2006, p. 4258-4272.

Qu, X.; Wu, D.; Mets, L.; Scherer, N. F., "Nanometer-localized multiple single-molecule fluorescence microscopy," Proc. Natl. Acad. Sc., vol. 101, No. 31, Aug. 2004, p. 11298-11303.

Los, Georgyi V., Ph.D., et al., "HaloTag Interchaneable labeling Technology for Cell Imaging and Protein Capture", found at http://www.promega.com/cnotes/cn011/cn011_02.htm.

Website of http://www.covalys.com/.

"Nano-Organized Polyelectrolyte Shells—Coating for Living Cells and Tissues", BioForum Europe 6, 51-59 (2005).

Hell, S. W. & Wichmann, J., "Breaking the diffraction resolution limit by stimulated emissions: stimulated-emission-depletion fluorescence microscopy," Opt. Lett. 19, 780-782 (1994).

Hell, S. W. & Kroug, M., "Ground-state-depletion fluorescence microscopy: a concept for breaking the diffraction resolution limit," Appl. Phys. B 60, 495-497 (1995).

Heintzmann, R., Jovin, T. M. & Cremer, C. J., "Saturated patterned excitation microscopy—a concept for optical resolution improvement," Opt. Soc. Am. A 19, 1599-1609 (2002).

Gustafsson, M. G. L., "Nonlinear structured-illumination microscopy: Wide-field fluorescence imaging with theoretically unlimited resolution," Proc. Nat. Acad. Sci. USA 102, 13081-13086 (2005).

Hell, S. W., Jakobs, S. & Kastrup, L., "Imaging and writing at the nanoscale with focused visible light through saturable optical transitions," Appl. Phys. A 77, 859-860 (2003).

Hell, S. W., "Far-Field Optical Nanoscopy," Science 316, 1153-1158 (2007).

Heisenberg, W., "The physical principles of the quantum theory.", pp. 16-17, (University of Chicago Press, Chicago, 1930).

Fölling, J. et al., "Angewandte Chemi", Angew. Chem. Int. Ed. 46, 6266-6270 (2007).

Bock, H. et al., "Two-color far-field fluorescence nanoscopy based on photoswitchable emitters," Appl. Phys. B 88 (2007), pp. 161-165.

Zondervan, R., Kulzer, F., Orlinskii, S. B. & Orrit, M., "Photoblinking of Rhodamine 6G in Poly(vinyl alcohol): Radical Dark State Formed through the Triplet," J. Phys. Chem. A 107, 6770-6776 (2003).

Bossi, M. et al., "Multicolor Far-Field Fluorescence Nanoscopy through Isolated Detection of Distinct Molecular Species," Nano Lett. 8, 2463-2468 (2008).

Dickson, R. M., Cubitt, A. B., Tsien, R. Y. & Moerner, W. E., "On-off blinking and switching behaviour of single molecules of green fluorescent protein," Nature 388, 355-358 (1997).

Reindl, S. & Penzkofer, A., "Higher excited-state triplet-singlet intersystem crossing of some organic dyes," Chem. Phys. 211, 431-439 (1996).

Ringemann, C. et al., "Enhancing Fluorescence Brightness: Effect of Reverse Intersystem Crossing Studied by Fluorescence Fluctuation Spectroscopy," ChemPhysChem, 612-624 (2008).

Eggeling, C., Widengren, J., Rigler, R. & Seidel, C. A. M., "Photobleaching of Fluorescent Dyes under Conditions Used for Single-Molecule Detection: Evidence of Two-Step Photolysis," Anal. Chem. 70, 2651-2659 (1998).

Donnert, G., Eggeling, C. & Hell , S. W., "Major signal increase in fluorescence microscopy through dark-state relaxation," Nat. Methods 4, 81-86 (2007).

Boyarskiy, V. P. et al., "Photostable, Amino Reactive and Water-Soluble Fluorescent Labels Based on Sulfonated Rhodamine with a Rigidized Xanthene Fragment," Chem. Eur. J. 14, 1784-1792 (2008).

Westermann, B. & Neupert, W., "Mitochondria-targeted green fluorescent proteins: convenient tools for the study of organelle biogenesis in Saccharomyces," Yeast 16, 1421-1427 (2000).

Griesbeck, O., Baird, G. S., Campbell, R. E., Zacharias, D. A. & Tsien, R. Y., "Reducing the Environmental Sensititivyt of Yellow Fluorescent Protein," J. Biol. Chem. 276, 29188-29194 (2001).

Lamesch, P. et al., "hORFeome v3.1: A resource of human open reading frames representing over 10,000 human genes," Genomics 89, 307-315 (2007).

Shroff, H., Galbraith, C. G., Galbraith, J. A. & Betzig, E., "Live-cell photoactibated localization microscopy of nanoscale adhesion dynamics," Nat. Methods 5, 417-423 (2008).

PCT International Preliminary Report on Patentability in co-pending related PCT application No. PCT/EP2009/056194, dated Sep. 9, 2010.

* cited by examiner

HIGH SPATIAL RESOLUTION IMAGING OF A STRUCTURE OF INTEREST IN A SPECIMEN

CROSS REFERENCE TO RELATED APPLICATIONS

This application is a continuation to International Patent Application No. PCT/EP2009/056194 entitled "High spatial resolution imaging of a structure of interest in a specimen", filed May 20, 2009, and claims priority to co-pending German Patent Application No. DE 1102008024568.2 entitled "Verfahren zum räumlich hochauflösenden Abbilden einer interessierenden Struktur einer Probe", filed May 21, 2008, and to European Patent Application EP 08 164352.0 entitled "High spatial resolution imaging of a structure of interest in a specimen", filed Sep. 15, 2008, now abandoned.

FIELD OF THE INVENTION

The present invention generally relates to a method for high spatial resolution imaging of a structure of interest in a specimen. More particular, the present invention relates to a method for high spatial resolution imaging of a structure of interest in a specimen in which the spatial resolution surpasses the diffraction barrier.

BACKGROUND OF THE INVENTION

WO 2006/127692 A2 has disclosed a method for high spatial resolution imaging of a structure of interest in a specimen, in which the structure of interest is marked with switchable fluorescent dyes in the form of so-called phototransformable optical markings. A subgroup of the markings is respectively activated into a state in which they can be excited to emit fluorescent light. The respective subgroup comprises so few of the markings that they lie at a distance from one another which is greater than the spatial resolution limit for imaging the specimen onto the sensor array. This makes it possible, after exciting the markings of the subgroup into fluorescence, to localize the origin positions of the fluorescent light with a resolution better than the diffraction limit which applies for the spatial resolution for imaging the specimen onto the sensor array, so that a point of the marked structure of interest is also respectively recorded with this increased resolution. The phototransformable optical markings are defined in WO 2006/127692 in that they can be switched on by an activating signal into a state in which they can be excited to emit fluorescent light. This activating signal may be the same as the excitation light which subsequently excites the markings into fluorescence. More specific embodiments of phototransformable optical markings, which are disclosed in WO 2006/127692, exclusively comprise photoactivatable fluorescent proteins, i.e. molecules which become a fluorophore only after they have absorbed at least one light quantum, or in other words they initially need to be switched on before they are fluorescent. The activating or switching process entails a modification of the molecular structure of the molecules (re-location of atom groups or even breaking or forming a bond). The method known from WO 2006/127692 is also referred to as PALM (Photoactivated Localization Microscopy).

A similar method known as STORM (Stochastic Optical Reconstruction Microscopy) and described by Rust et al. in Nature Methods, 3, 793-796 (2006) likewise uses molecules switchable into a fluorescent state, i.e. switchable fluorescent dyes, although these are not proteins but photoswitchable organic fluorophores, specifically the fluorescent dyes Cy3 and Cy5. It is known of these cyanine dyes that they can be switched between different conformational states, more specifically isomeric states.

A disadvantage of the PALM and Storm methods is that it is not possible in them to predict when the structure of interest in the specimen will be recorded to such a full extent that determining the position of further molecules will provide no additional useful information and the method may therefore be terminated.

A method for high spatial resolution imaging of a structure of interest in a specimen known as PALMIRA (PALM with Independently Running Acquisition), is described in C. Geisler, A. Schonle, C. von Middendorff, H. Bock, C. Eggeling, A. Egner and S. W. Hell: Resolution of .lamda./10 in fluorescence microscopy using fast single molecule photo-switching, Appl. Phys. A 88, 223-226 (2007. Here, a structure of interest in a specimen is marked with a switchable fluorescent protein. Specifically this is a protein by the name of rsFastLime, which by a light with a wavelength of 488 nm is not only excited into fluorescence in its initial state but also fractionally switched off into a nonfluorescent state and partially switched back again therefrom into its fluorescent state. The underlying mechanism is a conformational change of the fluorophore. These properties of the switchable fluorescent protein make it possible, with the light of only a single wavelength, alternately to set up subgroups of fluoresceable molecules of the protein in which the fluoresceable molecules lie at a mutual spacing greater than the diffraction limit, and to excite the fluoresceable molecules into fluorescence. It is thereby possible to continuously, i.e. with a high frequency, record images which register the alternating subgroups of the fluorescent molecules and in which the position of the respectively registered molecule can be determined with an accuracy beyond the diffraction limit. With the sum of the images, the structure in the specimen is recorded with a spatial resolution finer than the diffraction limit.

Switchable fluorescent proteins which are used by the methods explained above have for the first time been used in a method for high spatial resolution imaging of a structure of interest in a specimen called RESOLFT (Reversible Saturable OticaL Fluorescence Transition) which is described in US 2004/0212799 A1 and US 2006/0038993 A1.

The range of switchable proteins and fluorophores, which may be used for the RESOLFT, PALMIRA, PALM and STORM methods, is very small as compared to the total number of fundamentally known and available fluorescent dyes. Dyes which are both switchable and (in one of the switching states) capable of fluorescence, are very rare. They are therefore synthesized and optimized by elaborate methods. Added to this, the switching behavior and the fluorescent behavior depend very strongly on the chemical environment of the molecule. This applies both for switchable fluorescent proteins and for switchable organic fluorophores. This deficiency is to be regarded as fundamental, and it is associated inter alia with the fact that fluorescence and switching of the molecule are mutually competitive molecular processes which often compete with one another from the same excited state. The brightness of the switchable fluorescent dyes in their fluorescent state, i.e. the relative yield of fluorescent light from a molecule during repeated excitation, is also often only small compared with a multiplicity of nonswitchable organic fluorophores and nonswitchable fluorescent proteins. The strong restrictions due to switchable proteins or fluorophores, however, have to date being tolerated in order to obtain the high spatial resolutions achievable by the aforementioned methods for imaging structures of interest.

In so-called GSD (Ground State Depletion) microscopy (S. Bretschneider et al.: Breaking the diffraction barrier in fluorescence microscopy by optical shelving, Phys. Rev. Lett. 98, 218103 (2007)), the diffraction limit for imaging a structure marked by a fluorescent dye in a specimen is overcome by converting the respective fluorescent dye outside the respective measurement point from its electronic ground state, from which it can be excited into fluorescence by excitation light, into a dark electronic state in which it is not capable of fluorescence. This is done before exciting the remaining molecules at the measurement point into fluorescence by depopulating light with the same wavelength as the excitation light. The dark electronic state is typically a triplet state, while the ground state of the fluorescent dye is a singlet state. The molecules typically return thermally, i.e. not (optically) switched, from this dark state into the electronic ground state, so that only light of a single wavelength i.e. the excitation light is necessary for carrying out the experiment.

There still is a need for a method for high spatial resolution imaging of a structure of interest in a specimen which allows to make use of the resolution advantages of the methods known as PALMIRA, PALM and STORM but avoids their drawbacks with regard to the limited number of suitable switchable fluorescence dyes.

SUMMARY OF THE INVENTION

The present invention relates to a method for high spatial resolution imaging of a structure of interest in a specimen. This method has the steps of: selecting a substance from a group of substances, which have a first electronic state in which they can be excited by light of one wavelength to spontaneously emit fluorescent light, which can be converted from their first electronic state into a second electronic state by the light of the one wavelength, which can not be excited by the light of the one wavelength to spontaneously emit fluorescent light in their second electronic state, and which can return from their second electronic state into their first electronic state; marking the specimen's structure of interest with molecules of the substance; imaging the specimen onto a sensor array, a spatial resolution limit of the imaging being greater than an average spacing between closest neighboring molecules of the substance in the specimen; exposing the specimen to the light of the one wavelength in at least one region which has dimensions larger than the spatial resolution limit of the imaging of the specimen onto the sensor array at such an intensity that changing fractions of the molecules of the substance being in their first electronic state are, by the light of the one wavelength, excited to spontaneously emit fluorescent light and converted into their second electronic state, and that at least 10% of the molecules of the substance that are respectively in the first electronic state lie at a distance from their closest neighboring molecules in the first state which is greater than the spatial resolution limit of the imaging of the specimen onto the sensor array; registering the fluorescent light which is spontaneously emitted by the molecules of the substance in the region, in a plurality of images recorded by the sensor array during continued exposure of the specimen to the light of the one wavelength; and determining the position in the specimen of the molecules of the substance that are respectively in the first electronic state, which lie at a distance from their closest neighboring molecules in the first electronic state which is greater than the spatial resolution limit of the imaging of the specimen onto the sensor array, from the images recorded by the sensor array.

Other features and advantages of the present invention will become apparent to one with skill in the art upon examination of the following drawings and the detailed description. It is intended that all such additional features and advantages be included herein within the scope of the present invention, as defined by the claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. In the drawings, like reference numerals designate corresponding parts throughout the several views.

FIG. 2 (B) is a reconstruction which corresponds to a resolution-limited image of the same object as in FIG. 2 (A). The reconstruction was generated by the sum of the 61440 individual images. The small image at the bottom right in (B) shows a profile at the marked positions of FIGS. 2 (A) and (B), with the aid of which the resolution increase of the novel method may be seen clearly.

10 kW/cm$^2$ (a), 20 kW/cm$^2$ (b), 115 kW/cm$^2$ (c-e), 2.5 kW/cm$^2$ (f,g) at 532 nm (a-e) and 488 nm (f,g). Total number of events: 413,668 (green) and 39,694 (red) (a), 29,819 (green) and 176,443 (red) (b), 870,699 (c), 130,117 (d,e), 738,395 (f,g).

Figure 5:
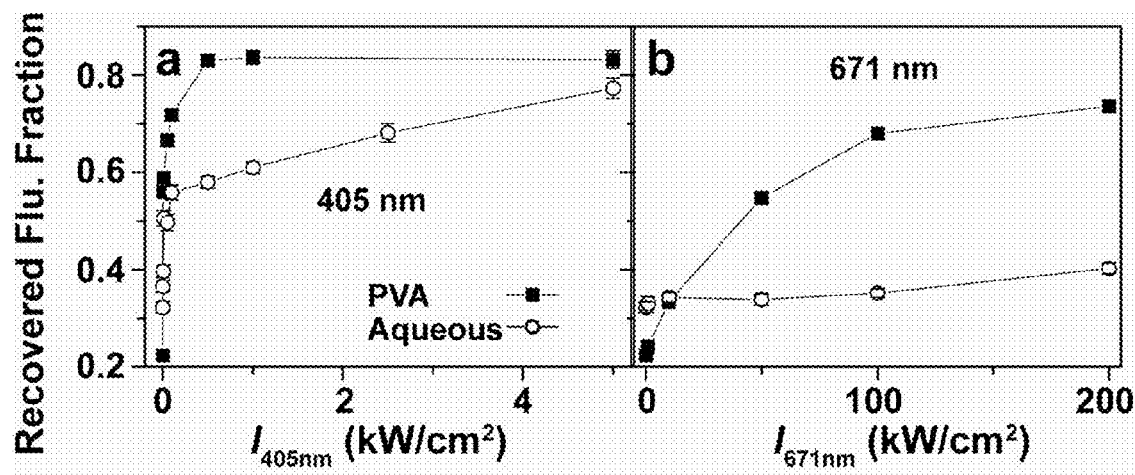

FIG. 5 illustrates an acceleration of the return of the fluorophores from the dark state to the bright singlet system and thus of the image acquisition in GSDIM microscopy by addition of 405 nm (a) or 671 nm (b) light; note that these wavelengths are outside the absorption maximum of the dye.

DETAILED DESCRIPTION

It is extremely surprising that even though it has essentially the same procedure as the method described as PALMIRA, the method of the invention does without switchable proteins or fluorophores. Instead, as a fluorescent dye in the new method, a substance is used in which the first and second states are different electronic states of the substance, i.e. states of the substance which differ from one another only in electronic terms. The substance then does not fall within the definitions of the substance used for the marking in US 2004/0212799 A1 and US 2006/0038993 A1, and it may be any conventional non-switchable fluorescent dye. Besides their electronic ground state from which they can be excited into fluorescence, practically all conventional fluorescent dyes have an electronic dark state into which they can be converted at a relevant rate owing to excitation with light of the same wavelength as can be used to excite the fluorescence. These are generally a singlet state as the fluoresceable ground state and a triplet state as the dark state. In normal fluorescent light microscopy, the fractional conversion of a fluorescent dye into its nonfluorescent triplet state instead of its excited singlet state—especially with high intensities of the excitation light—is known as a disadvantage because it reduces the yield of fluorescent light from a specimen. In the present invention, this effect is specifically utilized because the position of any individual molecule of the substance, with which the structure of interest in the specimen is marked, may be recorded with a resolution better than the diffraction limit only when the fluorescent light from the molecule can be registered in isolation, i.e. separately from the fluorescent light of neighboring molecules. To this end, only few of the molecules should respectively be in the first state.

In the new method of the present invention, it is often advantageous to implement measures which modify the lifetime of the nonfluorescent second state of the fluorescent dye in the specimen. In contrast to conventional fluorescence microscopy, however, this often involves extending rather than shortening the lifetime of the nonfluorescent second state. The measures which cause such extension of the lifetime include cooling the specimen to low temperatures at which thermal excitations are reduced to collision-induced transitions, reducing the concentration of oxygen in the specimen which quenches the triplet state of the fluorescent dye, for example with a glucose oxidase which binds oxygen or by making the measurements in a vacuum, or fixing or embedding the specimen in polymers, for example PVA. The increased lifetime of the nonfluorescent second state makes it possible to keep large fractions of the fluorescent dye in the nonfluorescent second state even with lower intensities of the light of the first wavelength.

Sometimes, however, it may even be advantageous in the new method to purposefully reduce the lifetime of the nonfluorescent second state of the fluorescent dye to increase the Intensity of fluorescence light gathered from the sample and to, thus, reduce the overall measuring time, particularly with low initial concentrations of the fluorescence dye. This may, for example, involve irradiating the sample with light of a second wavelength increasing the return rate of the fluorescent dye into its fluorescence state.

The known risk of photobleaching a conventional fluorescent dye from its triplet state likewise represents no problem in the new method. Strictly speaking, it is sufficient for a substantial fraction of the molecules of the fluorescent dye to return once into their fluorescent first state after they have been pumped into their nonfluorescent second state or differently fluorescent second state. After this return, the molecules are registered individually. Their subsequent fate is insignificant. For instance, they may enter the triplet state again and be photobleached therefrom.

Partial photobleaching of the fluorescent dye may even be carried out deliberately in the new method of the present invention, before the remaining unbleached molecules are registered. The new method can be carried out particularly advantageously when the molecules of the fluorescent dye do not exceed a particular spatial density in the specimen, because then a particular percentage of the molecules which remains in the first state likewise does not exceed a particular spatial density, which is essential for being able to register the individual molecules separately. If the actual concentration of the fluorescent dye in the specimen exceeds the particular spatial density, on the other hand, it may be difficult to register the molecules individually. In order to avoid this difficulty, the excess fluorescent dye may be permanently turned off by photobleaching by means of a high intensity of the light of the one wavelength or another wavelength, i.e. converted into a persistent dark state which differs from the first state and the second state. The persistent dark state, in which the fluorescent dye is no longer involved in the steps of recording the images for registering the individual molecules, typically differs not only electronically but for example also chemically from the first state and the second state which are used according to the invention for this registering of the individual molecules.

The new method of the present invention was carried out successfully with commercially available fluorescent dyes known as non-switchable to any person skilled in the art, such as Rhodamine 6G. Compared to conventional fluorescent light microscopy using this fluorescent dye—apart from different preferred details in the specimen preparation—in order to be carried out the intensity of the light of the one wavelength merely needs to be tuned with the frequency at which the images are recorded by the sensor array. The equipment requirements necessary for this are fullfilled by many fluorescent light microscopes. Here, it is only necessary to modify the control of the intensity of the light of the one wavelength according to the method according to the invention. As an alternative, the frequency of the image recording by the sensor array or the camera comprising the sensor array is altered. Accordingly, the new fluorescent light microscope is distinguished only by a special design of the control for the intensity of the light of the one wavelength. Preferably, online image processing is in this case provided for the individual images recorded by the sensor array.

This evaluation is expedient in order to adjust the intensity of the light of the one wavelength to such a value which actually makes it possible to register fluorescent light of individual molecules, spatially separated from one another, in the individual images. The value set for the intensity of the light of the one wavelength may be a constant value. This also includes a very fast pulse sequence with a frequency very much higher than the image frequency of the recorded images. The intensity of the light of the one wavelength may however also have an intensity profile temporally modulated with the sequence of the recording of the images, for example in order to deliberately set up the subgroup of the molecules of the substance which are in the first state, between the individual images, and to excite primarily the molecules of the set up subgroup into fluorescence during the recording of the individual images. Furthermore, the light of the one wavelength may in this case be directed onto the respective region of interest continuously (with the time-modulated intensity profile) or in pulses which are not resolved in the recording of the images (likewise with the time-modulated intensity profile).

The online evaluation of the individual recorded images may be used to determine the spatially inseparable fluorescent molecules of the substance, whereupon the intensity of the light may be varied until the density of such inseparable fluorescent molecules falls below a selected threshold (usually defining a lower threshold). The range of favorable intensities may further be defined by online evaluating the recorded images, determining the maximum density with which they show separable fluorescent molecules of the substance, and varying the intensity of the light such that a density threshold for such separable fluorescent molecules is reached from below (usually defining an upper threshold). This is desirable because on the one hand it is important for the molecules in the fluorescent state not to have a concentration so high that they can no longer be registered separately from one another, on the other hand, their concentration below this limit should be as high as possible so as to obtain as much information as possible about the structure of interest with each image. Also, the intensity of the irradiating light should be as high as necessary but as low as possible in order to avoid potential photodamage.

The initial exposure of the substance to the light of the one wavelength, which is primarily used to convert them essentially into their second state, may also be used to record an intensity distribution of the fluorescent light of all the substance in the specimen by the sensor array. This intensity corresponds to a concentration distribution of the substance in the specimen with the spatial resolution of the imaging of the specimen onto the sensor array.

This concentration distribution of the substance in the specimen represents an overview of the position of the structure of interest marked with the substance in the specimen. This simplifies the further steps of the new method, since it can thus for example be concentrated on to those regions of the specimen in which parts of the marked structure are actually present. This is usually not possible with switchable and above all activatable fluorophores since they are initially for the most part not in the fluorescent state, which prohibits an overview owing to the lack of signal.

Depending on the concentration distribution of the substance in the specimen, the intensity of the light of the one wavelength may also be adjusted for each region to be examined in more detail, or at least it may be preset to an approximately suitable value following fine adjustment. Furthermore, a local termination criterion for the recording of further images of the same region of the specimen may be defined on the basis of the concentration distribution of the substance in the specimen. The information content of additional images of a region of the specimen decreases, with the decrease in information content depending on the concentration of the substance in the respective region. If only very few molecules of the substance are present in a region, then relatively few images are sufficient in order to record the position of a high percentage of the molecules. Further images contribute only redundant information in this regard. The situation is different with a very high concentration of the substance in a region. Here, only smaller fractions of the substance in the specimen are recorded even with many images, and each further image makes new information available.

Specifically, in the new method, each position of a molecule as registered in the successive images may be entered not only into a high resolution overall image of the structure of interest in the specimen but, convoluted with the PSF (Point Spread Function) of the imaging of the specimen onto the sensor array or a derived function, it may also be entered into a reconstruction of the initially recorded intensity distribution. When this reconstruction has approximated the initially recorded intensity distribution or a derived distribution with certain fidelity, no significant further information about the structure of interest is to be expected with the positions of further molecules from further images. For the convolution with the PSF or related function, the brightness of the respective molecule may be taken into account as a weighting factor. Various values may be adopted as a measure of the similarity of the reconstruction to the initially recorded intensity distribution, for example a cross correlation, a simple difference or quadratic deviation of the normalized intensity distributions or deviations between the spatial frequencies (Fourier transforms) of the intensity distributions.

The new method is particularly well suited for marking the specimen's structure of interest with the non-switchable fluorophores by modifying a biological specimen with gene technology so that it itself expresses the non-switchable fluorescent dyes or specific binding sites for the non-switchable fluorescent dyes or for linkers coupled thereto. The structure of interest in the specimen is particularly advantageously marked in this way with non-switchable organic dyes via so-called small labels or self-labeling protein tags such as FlAsh, snap tags or halo tags. These and similar concepts are fundamentally known to the person skilled in the art, see for example http://www.promega.com/cnotes/cn011/cn011_02.htm or http://www.covalys.com/ or BioForum Europe 6, 51-59 (2005). This makes it possible to image proteins in a biological specimen with high resolution using widespread conventional fluorescent dyes.

For the fluorescent dye which is employed in the new method, it is not crucial for its second electronic state to be nonfluorescent, i.e. not capable of fluorescent and therefore entirely dark. It may also be differently fluorescent than the first electronic state. If the fluorescent dye is in this case excited into fluorescence in the second state by the same light as in its first electronic state, it is important that the fluorescent light which is emitted by the fluorescent dye in its first electronic state can be distinguished from the fluorescent light which is emitted by the fluorescent dye in the second electronic state.

It is to be understood that the new method may be combined with various measures which are familiar to the person skilled in the art, in particular from the field of methods known as PALM and STORM. These comprise in particular measures for three-dimensional resolution of the registered positions of the molecules in the specimen, i.e. for spatial resolution of these positions in the z direction as well. These measures include multi-photon excitation of the fluorescent dye from its first state, both for fluorescence and for transition into its nonfluorescent second state by focusing the exciting light of the one wavelength onto the respective plane of interest, and using two mutually opposing objectives with high numerical aperture in 4-pi configuration for exposing the specimen to the light of the one wavelength and/or for registering the fluorescent light from the specimen. In case the light is then focused only into one or more individual points of the plane, the plane is to be scanned with these points during all steps of the method, for example during the recording of each individual image. The focusing of the light of the one wavelength into individual points of the specimen may advantageously be combined with confocal registering of the fluorescent light from the specimen. As an alternative the specimen may be exposed, orthogonally to the direction of the imaging of the specimen onto the sensor array, with a light sheet of the light of the one wavelength formed e.g. by a cylindrical lens. This procedure is known to the person skilled in the art as SPIM (Selective Plane IlluMination).

A fluorescent light microscope for carrying out the new method differs from known fluorescence microscopes, in which a spatial resolution better than the diffraction limit is achieved, by the fact that there are no measures for finely spatially structuring any light from any light source; rather, a control of a light source for the light of the one wavelength only adjusts an intensity of the light of the one wavelength according to the new method.

At least one photodetector may additionally be provided, onto which a region of the specimen that corresponds to a plurality of pixels of the sensor array is imaged, in order to observe the chronological sequence of the emission of individual photons from this region. As already explained in connection with the new method, with such a photodetector it is possible to establish very rapidly, i.e. in particular even before the readout of the sensor array, whether the intensity of the measurement signal of only one or more molecules of the substance is registered in the respective region, for example in order to terminate the registering in favor of a new attempt if it is not found that the intensity comes from only a single molecule. This is very important in so far as the readout of a sensor array is often the rate-limiting factor for concluding a cycle of the new method. Sensor arrays suitable for carrying out the new method and the new fluorescent light microscope comprise CCD and preferably CMOS sensor arrays of conventional design. However, when selecting these it is necessary to ensure not only the possibility of fast readout but also that the dark noise and readout noise are small enough to obtain a good signal-to-noise ratio when carrying out the new method.

Figure 1:
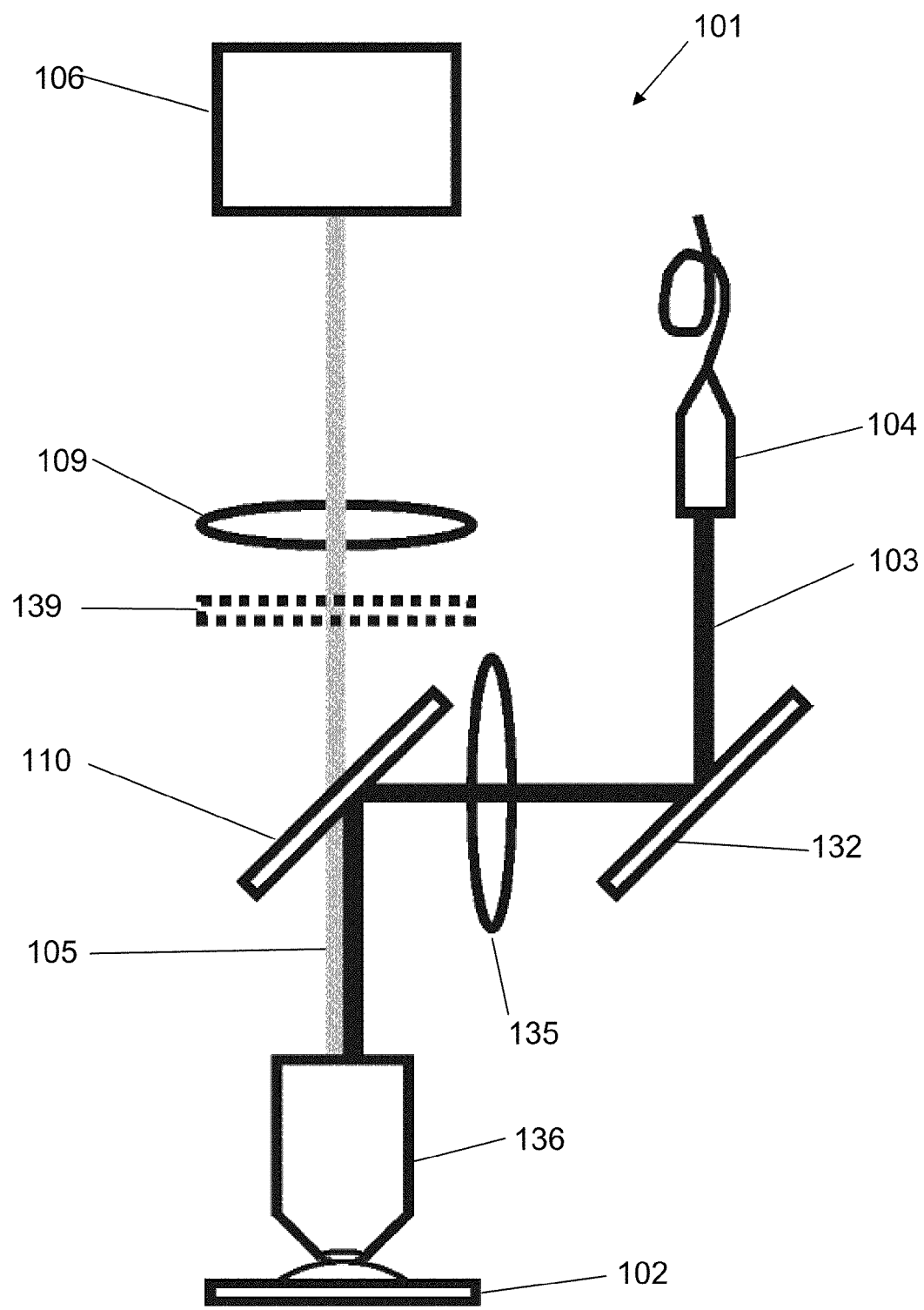
FIG. 1 schematically represents the structure of a fluorescent light microscope for high spatial resolution imaging of a structure of interest in a specimen according to the method of the present invention.

Now referring in more detail to the drawings, FIG. 1 schematically depicts a fluorescent light microscope 101. When carrying out the method according to the present invention for high spatial resolution imaging of a structure of interest in a specimen 102 with the fluorescent light microscope 101, light 103 of one wavelength (black line) from a light source 104 is provided via a mirror 132 and focused by means of a lens 135 into an objective 136. The light 103 is used for large-area illumination of an entire region of interest in the specimen 102. Fluorescent light 105 (gray line) from fluorescent dye in the specimen 102 is likewise collected by an objective, in this case the same objective 6, and separated from the light 103 by means of a dichroic mirror 110, and if necessary refined further by a suitable fluorescent light filter 139. In conjunction with the objective 135, a lens 109 ensures suitable imaging of the fluorescent molecules of the fluorescent dye onto a sensor array 106.

When carrying out a preferred embodiment of the method according to the invention using the fluorescent light microscope 101, the following steps are performed:

First, a structure of interest in a specimen is dyed with a non-switchable fluorescent dye.

The specimen is then embedded in a suitable environment. This may for example be PVA, or alternatively an aqueous medium (for example for living cells) from which oxygen is extracted. This measure is generally necessary since with modern technology and conventional fluorescent dyes, the lifetime of the dark triplets state in aqueous solutions without oxygen concentration reduction is not long enough to be able to separate individual molecule events. The oxygen reduction may for example be carried out by adding glucose oxidase and catalase. Such aqueous buffers are widely known media for microscopy. One medium, which is also suitable in principle for living cell applications, is:

88% (v/v) Gibco-DMEM (Invitrogen Corporation, Carlsbad, Calif.) with 10 mM HEPES, 10% (v/v) glucose oxidase (5 mg/ml, Sigma, G2133), 2% (v/v) catalase (2 mg/ml, Roche Applied Science, 106810).

Sometimes, when the marking density i.e. the spatial density of the fluorescent dye is too high, a sufficient fraction of the molecules of the fluorescent dye must be irreversibly bleached by suitable exposure of the specimen to the light before the start of the actual measurement. In any event, a sufficiently large fraction of the molecules must be pumped from their fluorescent first state into their dark second state by shining in the light before the start of the measurement, so that the images of the few molecules remaining in the fluorescent state on the sensor array lie further away from one another than the resolution limit on a sensor array. Typical intensities are between 1 and 100 $kW/cm^2$, depending on the environment and fluorescent dye. The intensity distribution of the fluorescent light, which can be recorded by the sensor array at the start of shining the light, shows the resolution-limited image of the structure of interest. This may subsequently be used as a reference for a termination criterion. In practice, for recording the resolution-limited image of the structure of interest, the exposure time or amplification of a camera comprising the sensor array may have to be adjusted, or an intensity filter may have to be used since the camera will usually be optimized for the detection single molecules. As an alternative, a light signal of low intensity may be used before the light signal, which is used to convert the multiplicity of the molecules into the dark state, in order to record a diffraction-limited reference image.

The actual measurement can be started without delay once a sufficient fraction of the molecules has been pumped into the dark state, and in any event this must be done within a period of time which is much shorter than the lifetime of the dark state. The optimal exposure time of the individual images is dictated by the average time over which a molecule, which is in the luminous first state, emits fluorescent light before it is converted back into the dark second state. In the examples used, this leads to a typical exposure time of 2 to 10 ms. During this time, on average in the order of 1000 photons are recorded on the detector from each molecule, before it is converted back into the dark state.

During the measurement, if molecules have been lost by irreversible bleaching, for example, the intensity of the light may be reduced in order to achieve an optimal density of the molecules which are in the first state.

The duration of the entire measurement is dictated by the number of individual images and their exposure time. The number of individual images required is dictated by the selected termination criterion. For more complex structures, typically up to 100,000 images individual are recorded. The total recording time is therefore of the order of minutes.

In the following, a particular embodiment of a method according to the present invention called Ground State Depletion microscopy followed by Individual Molecule return (GS-DIM) is explained in more detail:

Ground State Depletion Microscopy Followed by Individual Molecule Return (GSDIM)

The method relates to far-field fluorescence nanoscopy with ordinary fluorophores based on "switching" the majority of them to a metastable dark state, such as the triplet, and calculating the position of those left or which had spontaneously returned to the ground state. (As the term "switching" is used in a very general way here, it does not particularly refer to switchable fluorophores!) Continuous widefield illumination by a single laser and a continuously operating camera yielded dual-color images of rhodamine- and fluorescent protein-labeled (living) samples, proving a simple yet powerful super-resolution approach.

For many decades it was assumed that the resolution of any far-field optical microscope is limited to about half the wavelength of light. This perception has changed after the discovery that basic fluorophore transitions can be used for neutralizing the limiting role of diffraction[1,2]. More specifically, transitions that switch the fluorescence on or off enabled the sequential recording of objects that are much closer than the diffraction limit. Hence, not surprisingly, all far-field fluorescence nanoscopy modalities used so far rely on a time-sequential readout using a variant of fluorescence switching. In stimulated emission depletion (STED) microscopy[1], the fluorescence ability of the dye is switched using a de-excitation beam. In ground state depletion (GSD) microscopy[2,3], the fluorophores are switched to the dark triplet state. In contrast to STED, saturated patterned excitation microscopy (SPEM or SSIM)[4,5] switches the fluorescence to its maximum. All of these strategies have been extended to switching photoactivatable fluorescent proteins and photoswitchable (photochromic) organic fluorophores[6]. They all switch the fluorescence using a light distribution featuring either one or many intensity zeros that are translated in space, defining the coordinates at which fluorescence is on or off at a given point in time[7].

This is different in photoactivation localization (PALM)[8,9] or stochastic optical reconstruction microscopy (STORM)[10] where the fluorescence ability of the marker is switched stochastically in space, molecule by molecule. The fluorescence diffraction pattern of sparsely and randomly switched on (activated) molecules is recorded on a camera, allowing the calculation of their position with accuracy $\sim \Delta/\sqrt{m}$, with $\Delta$ denoting the width of the diffraction maximum and m the number of detected photons[11]. Clearly, for this concept to work, the molecules must cycle from a dark to a bright state, yielding m detectable photons, and then back to a dark state. Therefore, PALM and STORM use 'photoactivatable' proteins or organic compounds where the fluorescence ability of the molecule is elicited by the absorption of a photon. The energy provided by this 'activation' photon switches the fluorophore on, for example, by altering a chemical bond or an isomerization state. Examples of such compounds are the photoactivatable proteins EosFP[8] and PA-GFP[9], the 'caged' rhodamines[12] and the photoisomerizable cyanine dyes Cy3 and Cy5, which have been used both as activator-emitter pairs[10] as well as single photoactivatable labels[13,14].

Although they have provided stunning images, these photoactivatable compounds have limitations in terms of biocompatibility, labeling and switching performance. Additionally, they may call for dedicated activation lasers[8-10,12,14]. Last but not least, the apparent need for 'activatable' compounds narrows the scope of these techniques. The results reported here show that far-field fluorescence nanoscopy by stochastic single-molecule switching and localization can be performed without photoactivation, using basic transitions of standard markers: switching the fluorophores to their triplet state $T_1$ or another metastable dark state while recording those that are still left or have returned to the ground state $S_0$. Operating with ordinary fluorophores and rendering photoactivation either optional or obsolete, ground state depletion microscopy followed by individual molecule return (GSDIM) considerably expands the conceptual range and the applicability of far-field optical nanoscopy.

Figure 3:
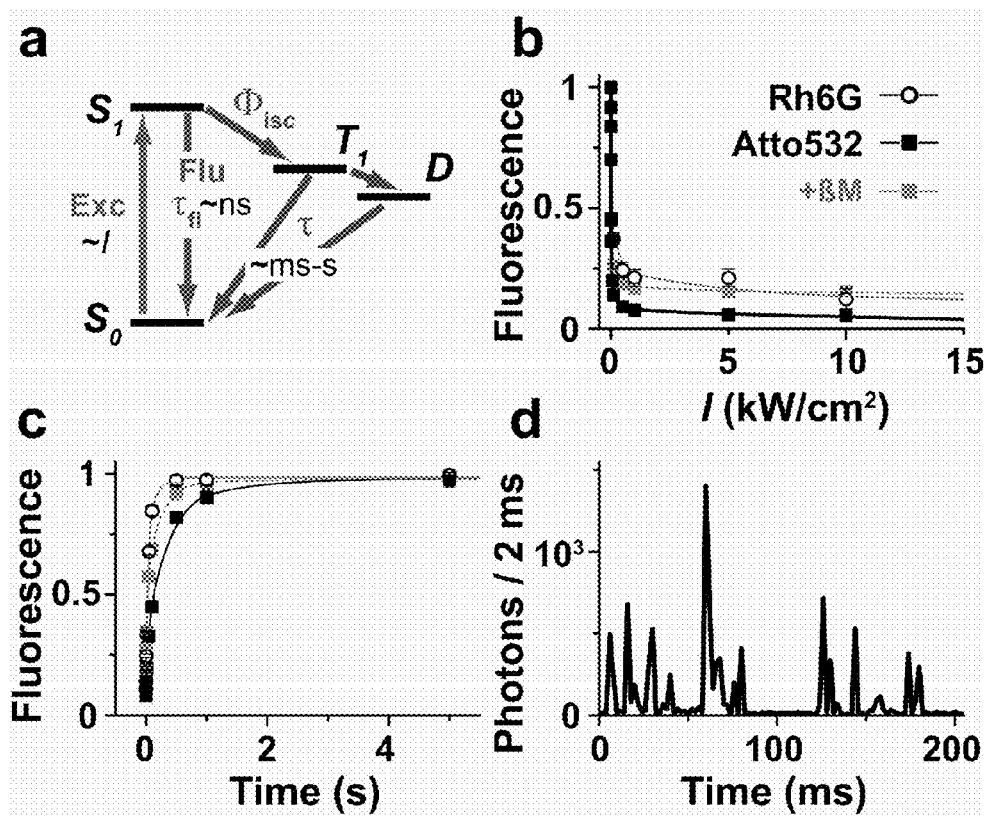
FIG. 3 illustrates how to "switch" a regular non-switchable fluorophore using its dark states. (a) Repetitive excitation (Exc) of the singlet ground state $S_0$ to the first excited singlet state $S_1$ elicits fluorescence (Flu) emission and "switches" a molecule to the triplet state $T_1$ or other dark states D with long lifetime ($\tau$). (b) Fluorescence light intensity emitted by the fluorescence dyes Rh6G, Atto532 and Atto532 plus a triplet quencher ($\beta$-mercaptoethanol; $\beta$M) conventionally used for increasing fluorescence light intensity) versus the Intensity of continous exitation light exiting the dyes for fluorescence. (c) Recovery of the active fluorophores after maximal dark state shelving (see Annex Table 1). (d) Fluorescence time trace of a single Atto532 molecule in PVA given as the number of detected photons per 2-ms time bin (I=115 kW/cm$^2$).

Having a lifetime ($\tau$) of $10^{-3}$ to 100 ms and being common in virtually all fluorophores, the lowest triplet state $T_1$ is the primary candidate for switching molecules[2]. In addition, $T_1$ serves as a gateway to other dark states D with similar or even longer $\tau$ of 1 to $10^4$ ms[15] (FIG. 3a). After the period $\tau$, the molecules return to $S_0$ where they can be repeatedly excited to the fluorescent state $S_1$, yielding the burst of m detectable photons required for computing their position. The same repeated excitation also switches the fluorophore off, because from $S_1$ the molecule crosses to $T_1$ with a typical probability $\Phi_{iSC} \leq 0.1\%$. If $\tau$ is $\sim 10^7$ times longer than the fluorescence lifetime ($\tau_{fl}$) of $\sim 3$ ns of $S_1$, a continuous wave illumination intensity $I > I_s \equiv h\nu/(\Phi_{iSC}\sigma\tau) \approx 1$ kW/cm$^2$ minimizes the fraction of $S_0$ molecules to $\epsilon \approx \tau_{fl}/\Phi_{iSC}\tau \ll 10\%$; $h\nu$ is the energy of the excitation photon and $\sigma$ the photon absorption cross-section of the molecule in $S_0$. Note that the minimal fraction $\epsilon$ of remaining $S_0$ molecules does not depend on I.

Owing to the presence of a larger dark-state population, the signal from a bulk of rhodamine dyes, specifically Rhodamine 6G (Rh6G) and Atto532 embedded in poly(vinyl-alcohol) (PVA), decreased with increasing intensity of the 532-nm excitation beam used (FIG. 3b). Notably, the majority fraction of the active dyes recovered within several tens of milliseconds (FIG. 3c). Addition of the triplet quencher 3-mercaptoethanol reduced $\tau$ and hence increased $\epsilon$. This experiment demonstrated the critical role of $T_1$ in the switching mechanism. On a single-molecule level the transient population of $T_1$ or D induced a fast stochastic on-off switching; the average on-times were a few milliseconds and the off-times were somewhat larger (FIG. 3d). The time spent in the fluorescent (on) singlet system was <10% of the total recording time. Yet, the number of photons detected per 2 ms on time amounted to m>500 because once they were back in the singlet system, the fluorophores emitted brightly, with the distribution of m peaking at 1,000 photons.

Dual-color GSDIM images of microtubule filaments and peroxysomes of mammalian cells (PtK2 line) embedded in PVA, immunolabeled with the rhodamine derivatives Atto532 (emission maximum $\sim$550 nm) and Atto565 (emission maximum $\sim$590 nm) showed the details absent in the conventional images (FIG. 4a,b). The images were recorded using a 532-nm continuous wave (CW) laser for both excitation and depletion, and a continuously running camera. The resolution of the GSDIM images was <30 nm (see Annex).

The disparity between the emission peaks of both dyes was only 40 nm. Nevertheless, they could be distinguished with a confidence >90% when comparing the signal of a single isolated emitter detected in a short-pass (<575 nm) channel with that in a long-pass (>590 nm) channel[16]. The conventional bulk recording requires mathematical unmixing.

The fact that the photon burst m is provided by the singlet system of a regular dye explains why m may easily exceed 500 photons. As $\epsilon \approx \tau_{fl}/\Phi_{iSC}\tau$, large values of $\tau$ and $\Phi_{iSC}$ of a fluorophore improve the switching, but a large $\Phi_{iSC}$ also reduces m which is approximated by $\eta_{det}\Phi_{fl}/\Phi_{iSC}$, and hence independent of I. ($\eta_{det}$ and $\Phi_{fl}$ denote the detection efficiency of the instrument and the fluorescence quantum yield, respectively.) Therefore, markers with $\Phi_{iSC} < 0.1\%$ and a large $\tau$ were used. The latter is provided by the PVA environment, which reduces the mobility of triplet-quenching oxygen and yields additional dark states[15]. Many fluorophores mounted in PVA, including Alexa488, Texas Red, FITC, Rhodamine110 and Oregon Green yielded $\epsilon \leq 10\%$ and $\tau$ greater than milliseconds; they all are suitable for GSDIM (Annex Table 1). m is likely larger than in genuine photoswitchable fluorophores because the probability of the latter to go to an off state is usually higher. GSDIM benefits from the fact that standard fluorophores are optimized for large fluorescence quantum yields.

Figure 2:
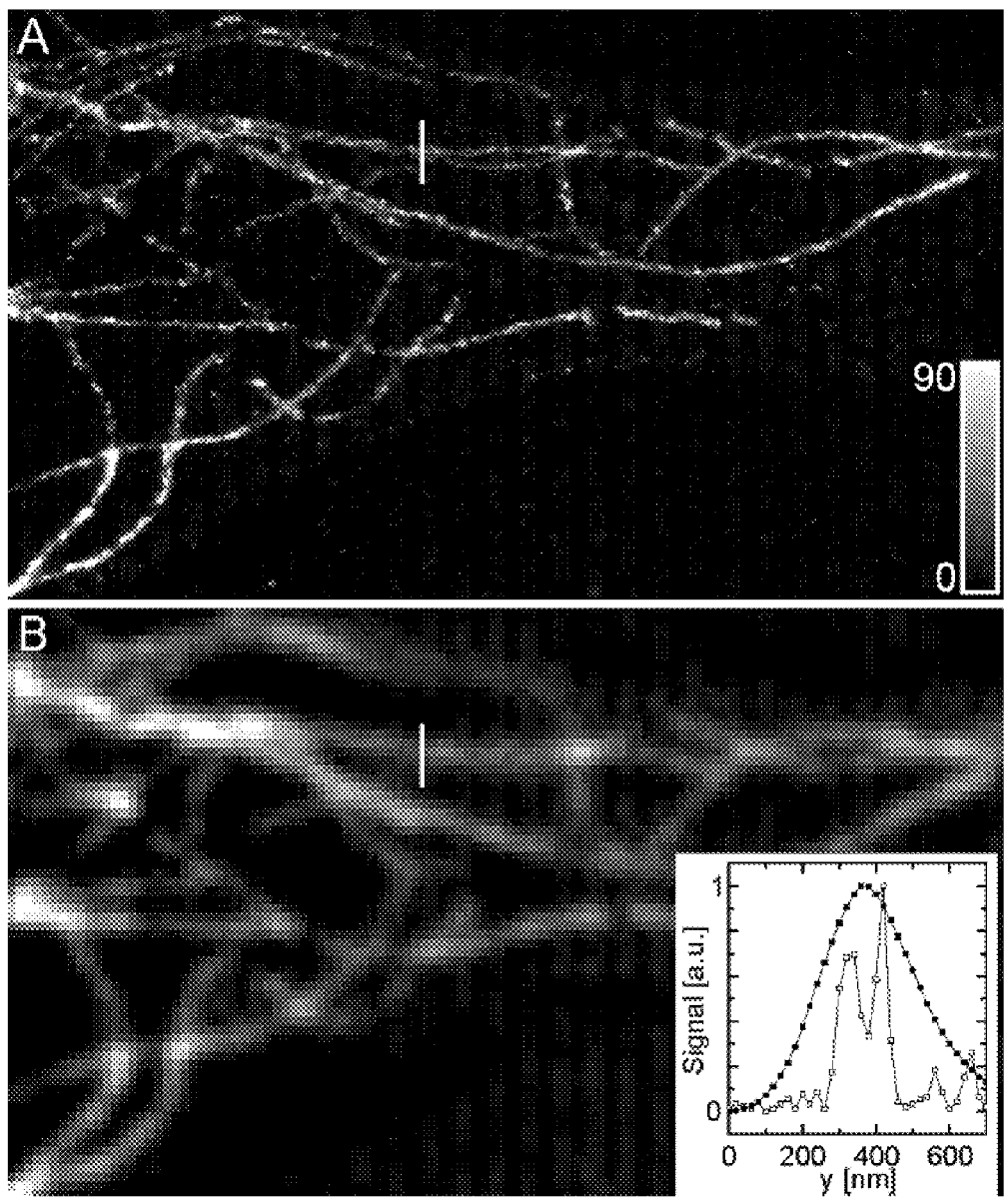
FIG. 2 (A) shows an overall image, recorded by the new method, of microtubuli of a PtK2 cell as the structure of interest. The structure is dyed with the dye rhodamine 6G. The medium, in which the cell is located, is an aqueous buffer solution with glucose oxidase and catalase (50 mM Tris, pH 7.5, 10 mM NaCl, glucose oxidase (Sigma, G2133), 40 µg/ml catalase (Roche Applied Science, 106810), 10% (w/v) glucose). The number of individual images recorded for the overall image is 61440 with exposure times of 5 ms. The light intensity was constant at 50 kW/cm$^2$.

Next, the samples were immersed in an aqueous solution containing an oxygen scavenger which, by increasing $\tau$ from about microseconds to ~10-100 ms, enabled $\epsilon < 10\%$ (Annex Table 1). The GSDIM images of microtubules immunostained with Rh6G immersed in TRIS buffer containing glucose oxidase as oxygen scavenger displayed a superior resolution (FIG. 2c). Notably, GSDIM was also possible in cellular media such as HEPES-buffered Dulbecco's modified Eagle's medium (HDMEM) with an oxygen-scavenging system. Clusters of integrin-β-3 of human glioma cells labeled with Atto532 were far better resolved by GSDIM than by the conventional recording (FIG. 4d,e).

Fluorescent proteins can also be efficiently transferred to a metastable dark state such as the triplet or different protonation states[17]. All fluorescent proteins tested, namely EGFP, EYFP, Citrine and PhiYFP had $\epsilon \leq 10\%$ and $\tau > 1$ ms in aqueous media and were thus suitable for GSDIM (Annex Table 1). The GSDIM image of living PtK2 cells expressing Citrine fused to the mictotubule-associated protein Map2, resulting in the labeling of the microtubule cytoskeleton, illustrates a marked resolution gain by GSDIM in comparison with the conventional widefield image (FIG. 4f,g), yet the resolution (~40 nm) and the contrast were still somewhat lower than in a recording relying on immunostaining (FIG. 4a-e). This stems from the fact that switching to the dark state is usually faster for the fluorescent proteins than for the organic dyes, restricting the number m of photons in a bunch (see Annex Methods). Furthermore, the average off-time of a Citrine molecule in this molecular construct is rather long (>1 s; Annex Table 1), which limits the number of on-off cycles before irreversible bleaching. As a result, the contrast of the reconstructed GSDIM image is also reduced. In comparison, Rh6G molecules return faster, are more photostable and return more often. Nevertheless, the stronger photobleaching of Citrine seems not to be of fundamental nature because the lifetime of the dark state of these proteins in a pure aqueous environment is much shorter (50 ms), implying that Citrine is generally more photostable than the proteins in the example above. Although the substantial variation in lifetime can be attributed to changes in the pH or in the concentration of molecular oxygen (Annex Table 1), this example highlights the relevance of the molecular environment in a particular application of GSDIM.

Fluorescence depletion, instead of activation, provides a conventional first image, giving an overview of the sample and an indication when to stop the stochastic picture assembly. As less than one singlet-state molecule was allowed to be present in the diffraction area, the allowable total number of usable fluorophores within this area was $1/\epsilon \approx \Phi_{iSC} \tau/\tau_{fl}$, which is a function of the dye and the environment. A remedy for densely labeled samples is to bleach some of the fluorophores before imaging (FIG. 4) or shelve them in a very long-lived dark state. Likewise, the return rate $1/\tau$ of the few, remaining fluorophores may be too low at later camera frames, slowing down the image acquisition. In this case, the return can then be accelerated by additional light depopulating the dark state ($T_1$ or D) via dark-state absorption[17] (FIG. 5). This procedure was applied by adding 375-nm light in the recordings of FIG. 4 starting from image frame number ~20,000 in FIG. 4a, and number ~10,000 in FIGS. 4b and 4e; no additional light was used in the recordings of FIGS. 4c and 4g. Note that this type of activation is optional and still applied to regular fluorophores. As it records molecules individually, GSDIM requires a fluorophore to recover to $S_0$ only once.

In conclusion, far-field fluorescence nanoscopy based on switching individual emitters with elementary fluorophore transitions has been demonstrated. Excitation followed by crossing to a metastable triplet (dark) state switched the markers off, whereas their spontaneous return to the ground state switched them back on, eliciting the burst of photons required for calculating their position. By stochastically recording the position of individual molecules, GSDIM substantially differs from GSD microscopy (which defines the position of emitters using a zero of the switching light intensity). Yet both concepts rely on the same molecular mechanism, a fact that highlights switching between a dark and a bright state as the actual element enabling the super-resolution imaging.

In any case, the intensity-zero, ensemble-based approach and the stochastic single-molecule-based approach remain complementary modalities of determining the position of nearby molecules. The latter modality has the advantage of requiring fewer switching cycles, which also accounts for the fact that GSDIM currently appears to be more readily applicable than GSD microscopy. Moreover, GSDIM is strikingly simple: continual epifluorescence recording with a freely operating camera allows the computational construction of nanoscale images with multiple standard dyes and fluorescent proteins.

REFERENCES

1. Hell, S. W. & Wichmann, J. *Opt. Lett.* 19, 780-782 (1994).
2. Hell, S. W. & Kroug, M. *Appl. Phys. B* 60, 495-497 (1995).
3. Bretschneider, S., Eggeling, C. & Hell, S. W. *Phys. Rev. Lett.* 98, 218103 (2007).
4. Heintzmann, R., Jovin, T. M. & Cremer, C. J. *Opt. Soc. Am. A* 19, 1599-1609 (2002).
5. Gustafsson, M. G. L. *Proc. Nat. Acad. Sci. USA* 102, 13081-13086 (2005).
6. Hell, S. W., Jakobs, S. & Kastrup, L. *Appl. Phys. A* 77, 859-860 (2003).
7. Hell, S. W. *Science* 316, 1153-1158 (2007).
8. Betzig, E. et al. *Science* 313, 1642-1645 (2006).
9. Hess, S. T., Girirajan, T. P. K. & Mason, M. D. *Biophys. J.* 91, 4258-4272 (2006).
10. Rust, M. J., Bates, M. & Zhuang, X. *Nat. Methods* 3, 793-796 (2006).
11. Heisenberg, W. *The physical principles of the quantum theory.* (University of Chicago Press, Chicago, 1930).
12. Fölling, J. et al. *Angew. Chem. Int. Ed.* 46, 6266-6270 (2007).
13. Bock, H. et al. *Appl. Phys. B* 88 (2007).
14. Heilemann, M. et al. *Angew. Chem.* 47, 6172-6176 (2008).
15. Zondervan, R., Kulzer, F., Orlinskii, S. B. & Orrit, M. *J. Phys. Chem. A* 107, 6770-6776 (2003).
16. Bossi, M. et al. *Nano Lett.* 8, 2463-2468 (2008).
17. Dickson, R. M., Cubitt, A. B., Tsien, R. Y. & Moerner, W. E. *Nature* 388, 355-358 (1997).

ANNEX

FIG. 5 shows the fraction of the fluorescence signal that has recovered after ground state depletion of Atto532 in PVA (black squares) and of Atto532-immunostained microtubuli in PtK2 cells embedded in aqueous buffer containing an oxygen scavenging system (open circles). The fluorescence recovery in the probe-pump-probe mode was measured. The first probe pulse (532 nm) established the reference signal before the depletion. The depletion was effected by a 10 ms pulse (532 nm) of focal intensity I=1 kW/cm$^2$ for PVA and 100 kW/cm$^2$ for the aqueous solution, followed by the second probe pulse (532 nm), lasting for 0.5 ms and producing I=100 W/cm$^2$. The second probe pulse was delayed by 10 ms with respect to the depletion pulse. Illumination with 405 nm light of intensity $I_{405\,nm}$ (a) and of 671 nm light of intensity $I_{671\,nm}$ (b) in the period between the pump and the second probe pulse increased the fraction of fluorescence recovering in the time period between the depletion and the second probe pulse as plotted above. Absorption of 405 nm or 671 nm light of the dyes in their dark states may induce dark state depopulation via higher excited states, as observed for reverse intersystem crossing[1,2]. The effect may be stronger in PVA due to stronger dark state absorption and reverse crossing to the singlet system and/or due to the presence of multiple long lasting dark states.

ANNEX TABLE 1

Parameters of optical dark-state shelving for several standard fluorophores: maximum dark state population [D] and dark state recovery time τ

| Fluorophore | Environment | [D] [%] | τ[ms] |
|---|---|---|---|
| Rh6G [1] | PVA | 90 | 45 |
|  | aqueous | 87 | 170 |
| Rh110 [2] | PVA | 81 | 1.5 |
| Rh123 [2] | PVA | 90 | 17 |
| Rh-sart3b [1] | PVA | 93 | 290 |
| Rh-sart3f [1] | PVA | 96 | 390 |
| Atto532 [1] | PVA | 95 | 230 |
|  | aqueous | 90 | 60 |
| Atto565 [3] | PVA | 94 | 190 |
| Alexa488 [2] | PVA | 90 | 10 |
| Oregon Green [2] | PVA | 96 | 7 |
| Texas Red [2] | PVA | 95 | 5 |
| FITC [2] | PVA | 78 | 0.5 |
| Bodipy [2] | PVA | 94 | 6 |
| EGFP [2] | aqueous | 95 | 50 |
| EYFP [2] | aqueous | 95 | 50 |
| Citrine [2] | aqueous | 90 | 50 |
|  | microtubule (Map2) in live cell | 85 | 1000 |
| PhiYFP [2] | aqueous | 97 | 40 |

The dark state population [D] and recovery time τ were determined from the fluorescence signal detected on a dye ensemble in pump-probe measurements. The time dependence of the recovery data follows a stretched exponential ($\sim\exp(-(t/\tau)^\alpha)$) with exponents α=0.6-0.8 significantly deviating from mono-exponential recoveries (α=1), and indicating several dark states[3,4]. For the organic dyes (see table until Bodipy) measurements in PVA on the pure dyes and those in aqueous environment on immunostained microtubules in PtK2 cells with a buffer containing an oxygen scavenging system were performed. For the fluorescent proteins EGFP, EYFP, Citrine and PhiYFP the measurements were performed on purified proteins fixed on glass surface by Poly-L-Lysine and covered with PBS buffer (aqueous). In the case of Citrine the results of the measurements performed in cells were added applying the samples shown in FIG. 2f,g. Excitation at [1]532 nm, [2]488 nm, and [3]561 nm. The reason for the vast increase in τ of Citrine in cells compared to pure aqueous environment may result from a change in pH or concentration of molecular oxygen, both influencing the characteristics of dark states of the fluorescent protein such as the triplet state or different protonation states[4]. The longer lifetime τ of the dark state of Citrine in cellular environment also increases the probability of photobleaching. A prominent pathway of photobleaching is the absorption of photons in the fluorophore's dark state and thus the excitation to higher excited energy levels of high reactivity[5,6].

ANNEX METHODS

Fluorescent dyes. The fluorescent dyes Rhodamine6G (Rh6G), Rhodamine110 (Rh110), Rhodamine123 (Rh123), Atto532, Atto565, Alexa488, Oregon Green 488, Texas Red, Fluorescein-isothiocyanate (FITC), and Bodipy (FL) were purchased from different suppliers (MoBiTec, Gottingen, Germany; AttoTec, Siegen, Germany; Sigma-Aldrich; Invitrogen; or Radiant Dyes, Wermelskirchen, Germany). The rhodamine derivatives Rh-sart3b and Rh-sart3f (sulfonated rhodamines with a rigidized xanthene fragment, obtained from 1,2,3,4-tetrahydroquinolin-7-ol) were presented in reference [7] as compounds 3b and 3f. For ensemble measurements in poly(vinyl-alcohol) (PVA), the buffered stock solution of the dyes was diluted in (5%) PVA to a final dye concentration of ~10$^{-6}$ M and spin-coated the PVA samples on microscope cover glass. Where marked, 10% (v/v) of β-mercapto-ethanol (Fluka) was added prior to spincoating.

Cell culture and immunocytochemistry. The mammalian PtK2 cell line applied was grown as previously described[8]. The cells were seeded on standard glass coverslips to a confluence of about 80% and let them grow at 37° C. in a water-saturated atmosphere of 5% $CO_2$. Fixation was performed with cold methanol (−20° C.) for 4 min, followed by incubation in blocking buffer (PBS containing 1% BSA w/v). The microtubules were stained with anti-β-tubulin mouse IgG (Sigma) and the corresponding dye conjugated to sheep anti-mouse IgG (Sigma). The peroxysomes were labeled with anti-PMP70 rabbit IgG (Abcam) and Atto532-conjugated sheep anti-mouse IgG or Atto565-conjugated goat anti-rabbit IgG. Imaging of the immunostained cells was either performed in PVA (spincoating of 1% PVA in PBS (pH 7.4) solution at 3000 rpm) or in standard aqueous imaging buffer (50 mM Tris, pH 7.5, 10 mM NaCl, 0.5 mg/mL glucose oxidase (Sigma, G2133), 40 µg/mL catalase (Roche Applied Science, 106810) and 10% (w/v) glucose). The images of FIG. 2d,e were taken from human U373 MG glioma cells. The human glioma cell line U373MG was grown in RPMI Glutamax, high glucose (Gibco) supplemented with 10% FBS, 100 U/ml penicillin, 100 µg/ml streptomycin and 1 mM sodium pyruvate. Cells were seeded and fixed as described above. Immunostaining of integrin-β-3 has been performed using anti-integrin-β-3 IgG as primary and Atto532-conjugated sheep anti-mouse IgG antibody as secondary antibody. The sample was embedded in standard growing medium (DMEM, high glucose, HEPES 10 mM) with addition of 10% (v/v) of glucose oxidase (5 mg/ml) and 2% (v/v) catalase (2 mg/ml). While this medium is compatible with live cell measurements, cell fixation was required to prevent clustering of integrin-β-3 due to the antibody labeling.

Fluorescent Proteins.

Protein purification. Plasmids coding for the fluorescent proteins EGFP[9], EYFP (Clontech, Mountain View, Calif.), Citrine[10] and PhiYFP (Evrogen, Moscow, Russia) were transformed into *Escherichia coli* BL21CodonPlus RIL (Stratagene, La Jolla, Calif., USA). For protein expression, cells carrying the plasmids were grown to an OD600 of 0.6 in LB medium containing 100 µg/ml ampicillin and were induced with 1 mM isopropyl-1-thio-L-D-galactopyranoside. Following 6 h incubation at 25° C. the resultant biomass was pelleted by centrifugation, resuspended in PBS with protease inhibitors and sonicated. The bacterial lysate was cleared by centrifugation, and fluorescent proteins were affinity purified from the supernatant on a Ni-nitrilotriacetic acid (NTA)-agarose column (Qiagen, Hilden, Germany). For ensemble measurements, 100 μl of Poly-L-Lysine solution (Sigma-Aldrich, Steinheim, Germany) was coated on a microscope cover slip. After short rinsing with water, 50 μl of the protein solution (in PBS pH 7.4) were added. After one hour, unbound proteins were shortly rinsed off with water and 10 μl of PBS (pH 7.4) was added. Finally, the sample was sealed with silicone glue.

Plasmid construction. Standard methods were used for cloning. To tag the microtubule associated protein Map2 at its N-terminus with Citrine, the expression plasmid pSEMS-Citrine-Map2 was constructed by Gateway vector conversion (Invitrogen, Carlsbad, Calif., USA) from the donor vector pDONR223-Map2[11] and the empty destination vector pSEMS-Citrine, a modified version of pSEMS-SNAP26m-Gateway (Covalys Biosciences, Witterswil, Switzerland).

Cell culture, transfection and mounting of the cells. For transfection, PtK2 cells were grown overnight on glass cover slips. After reaching ~80% confluence, the plasmid pSEMS-Citrine-Map2 was introduced (Nanofectin kit, PAA, Pasching, Austria). One day after transfection, cells expressing Citrine-Map2 were visible. Typically they were imaged within the following day. For microscopy, cells were rinsed with cell culture medium without phenol red. Finally, the living cells were mounted with pre-warmed Ringer's solution (8.6 g/l NaCl, 0.3 g/l KCl, 0.33 g/l $CaCl_2$) and sealed with silicone glue.

Fluorophore characterization. The ensemble measurements were performed on an inverse fluorescence microscope (DM IRB, Leica Microsystems, Mannheim, Germany) with circularly polarized, continuous-wave laser light of 488 nm (Ar—Kr laser Innova 70C-5, Coherent, Santa Clara, Calif.), 532 nm (DPSS GL-150-A3, HB Laser, Schwäbisch Gmünd, Germany), 561 nm (DPSS Cobolt Jive 50, Cobolt, Stockholm, Sweden), 405 nm (DPSS BCL-030-405-S, CrystaLaser, Reno, Nev.) and/or 671 nm (DPSS Monolas-671-300MM, Alphalas, Göttingen, Germany), with an oil immersion objective lens (HCX PL APO 100x/1.4 oil, Leica) for creating an ~2-3 μm large excitation spot, and with detection in epi-direction on an avalanche photo diode (SPCM-AQR-13F, Perkin-Elmer Optoelectronics, CA). The switching and the power of the lasers were controlled by an acousto-optical tunable filter (AOTF; AA.AOTF.nC, Pegasus Optik, Wallenhorst, Germany). The residual level of fluorescence was determined after shelving the molecules in the dark state, as well as the recovery from the dark state in a probe-pump-probe mode with probe pulses (0.5 ms, I=100 $W/cm^2$) before and after the pump pulse (≈1 ms) of varying intensity (10-100 $kW/cm^2$); the probe pulse arrived either immediately or after a certain time delay after the pump pulse. The normalized fluorescence signal is given by the ratio of both probe signal levels. The fluorescence depletion curve of FIG. 3b represents an upper bound for the fraction $\epsilon$ of residual singlet state molecules, i.e., the actual depletion is more efficient.

Imaging. The high-resolution images were recorded on a home-built setup described previously[8,12]. The microscope is equipped with a continuous-wave 532 nm (VERDI V5, Coherent Inc., Santa Clara, Calif., USA) or a continuous-wave 488 nm (Ar—Kr laser Innova 70C-5, Coherent), and a continuous-wave 375 nm laser (iPulse-375, Toptica Photonics AG, Gräfelfing, Germany), with an oil immersion objective lens (HCX PL APO 100x/1.4 oil, Leica) for creating an ~12 μm large excitation spot, and with detection in epi-direction on an EM-CCD camera (IXON-Plus DU-860, Andor Technology, Belfast, Northern Ireland). For the two-color measurements, the detection path was split by a dichroic mirror (z570DCXR, AHF Analysentechnik, Tübingen, Germany) onto two separate parts of the camera. Additional wavelength selection was implemented by appropriate band-pass filters (585/75 and 630/75, respectively). Localization and color assignment of the single molecules as well as linear unmixing of the diffraction-limited images was performed as described in references [8,12].

Due to the stochastic nature of the photon emission and dark state transition, the number of photon counts detected from a single molecule fluctuates, i.e., the different single spots detected in the camera frames are not equally intense. A minimum number of photon events for a proper single-molecule assignment was introduced. Such thresholding minimizes wrong molecular assignments due to autofluorescence or other background sources. The threshold in photon counts was 560 in FIG. 4a,b, 400 in FIG. 4c,d, and 80 in FIG. 4g.

The resolution of the final GSDIM images were experimentally assessed from determining the size of the blurring of a point-like object. Such point-like objects most probably represented single (unspecifically bound) fluorescent antibodies or proteins. The difference in resolution (<30 nm in FIG. 4a-c,e and <40 nm in FIG. 4g) stems from differences in the average number m of photons detected per single-molecule on-event (~1600 in FIG. 4a,b, ~2000 in FIG. 4c, ~2600 in FIG. 4e, and ~800 in FIG. 4g), which is determined by the quantum yield of the fluorophore and the average time before turning dark. The magnitude of m also influences the level set for the above-mentioned photon number threshold, and gives a theoretical estimate of the expected localization accuracy $\Delta/\sqrt{(m/2)}$ of the GSDIM imaging process, with $\Delta$=250 nm denoting the width of the diffraction maximum (<18 nm in FIG. 4a-c,e and <40 nm in FIG. 4g). (Due to the readout noise of the EM-CCD camera, a factor of ½ for a proper calculation of the theoretical localization accuracy ($\Delta/\sqrt{(m/2)}$ has to be included[12]). Besides the localization accuracy, experimental characteristics such as the signal-to-noise ratio or slight sample drifts may further influence the resolution of the images, most probably accounting for the difference in the values of experimental resolution and theoretical localization accuracy.

Figure 4:
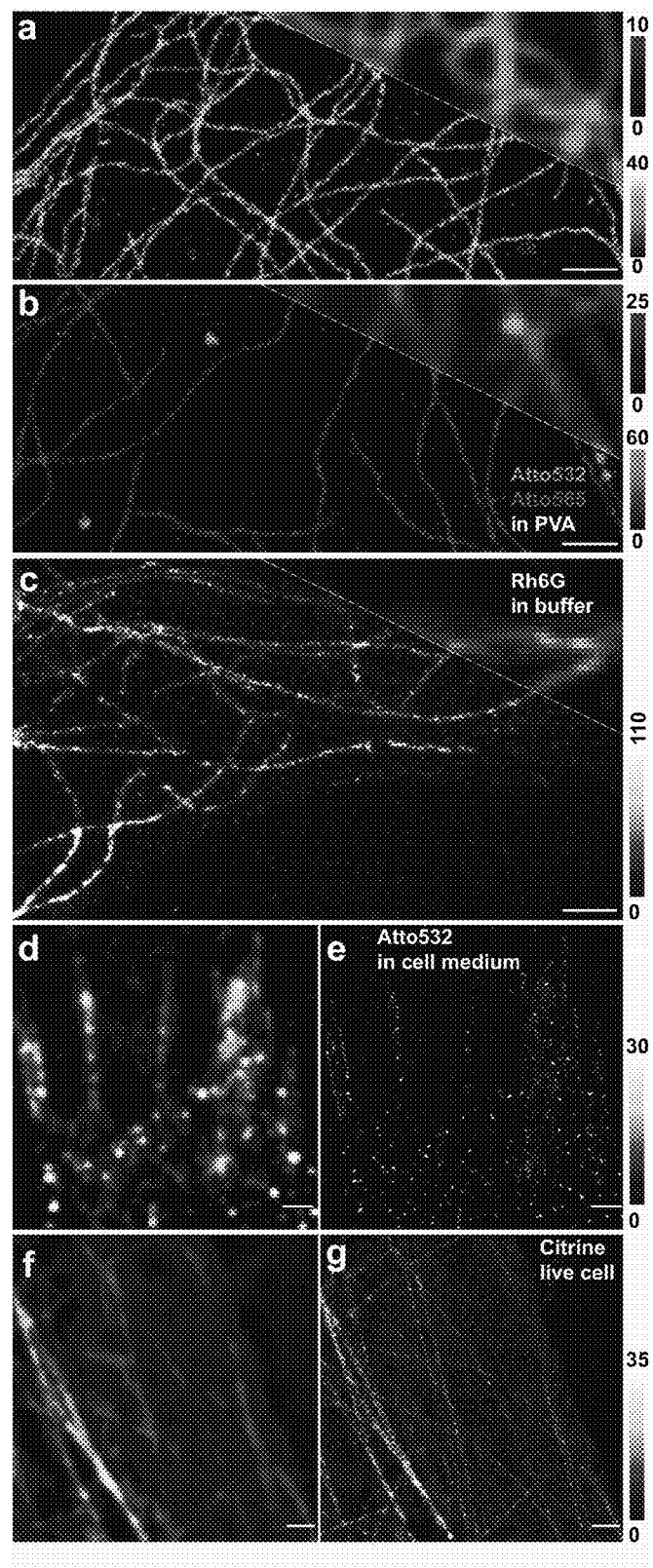
FIG. 4 shows subdiffraction resolution images recorded by a method according to the present invention called Ground State Depletion microscopy followed by Individual Molecule return (GSDIM). (a,b) GSDIM images of immunostained (Atto532, green or Atto565, red) microtubules and peroxysomes of PtK2-cells embedded in PVA. Epifluorescence images are shown in the upper right corners. In (b) the fluorophore labels are reverted with respect to (a). (c) Immunostained (Rh6G) microtubules of PtK2-cells in aqueous buffer. (d,e) Diffraction-limited (d) and GDSIM (e) recordings of immunostained (Atto532) integrin-$\beta$-3 clusters of human glioma cells in a cell medium. (f,g) Epifluorescence (f) and GSDIM (g) images Microtubule cytoskeleton of living PtK2 cells labeled with Citrine-Map2. Scale bars, 1 µm. Color bars indicate the number of events localized per spot. Number of camera frames: 72,000 (a), 82,000 (b), 61,000 (c) and 31,000 (d-g); the epifluorescence images were obtained by adding the total signal of all the frames. Camera frame rate: 100 Hz (a,b), 200 Hz (c-g). Laser intensity and wavelength.

The experimental resolution was determined from GSDIM images of 10 nm pixilation, to ensure proper determination. For proper resolving of objects, the image pixilation has to be smaller than half the desired resolution[13]. The (immuno) labeled structures (microtubule or integrin clusters) presented in the GSDIM images of FIG. 4 are usually larger than 50 nm. As a consequence, a pixilation of 20 nm has been applied in the shown images, which is more adequate for visual presentation of the objects imaged here.

ANNEX REFERENCES

1. Reindl, S. & Penzkofer, A. *Chem. Phys.* 211, 431-439 (1996).
2. Ringemann, C. et al. *Chem Phys Chem,* 612-624 (2008).
3. Zondervan, R., Kulzer, F., Orlinskii, S. B. & Orrit, M. *J. Phys. Chem. A* 107, 6770-6776 (2003).
4. Dickson, R. M., Cubitt, A. B., Tsien, R. Y. & Moerner, W. E. *Nature* 388, 355-358 (1997).
5. Eggeling, C., Widengren, J., Rigler, R. & Seidel, C. A. M. *Anal. Chem.* 70, 2651-2659 (1998).
6. Donnert, G., Eggeling, C. & Hell, S. W. *Nat. Methods* 4, 81-86 (2007).
7. Boyarskiy, V. P. et al. *Chem. Eur. J.* 14, 1784-1792 (2008).

8. Fölling, J. et al. *Angew. Chem. Int. Ed.* 46, 6266-6270 (2007).
9. Westermann, B. & Neupert, W. *Yeast* 16, 1421-1427 (2000).
10. Griesbeck, O., Baird, G. S., Campbell, R. E., Zacharias, D. A. & Tsien, R. Y. *J. Biol. Chem.* 276, 29188-29194 (2001).
11. Lamesch, P. et al. *Genomics* 89, 307-315 (2007).
12. Bossi, M. et al. *Nano Lett.* 8, 2463-2468 (2008).
13. Shroff, H., Galbraith, C. G., Galbraith, J. A. & Betzig, E. *Nat. Methods* 5, 417-423 (2008).

Many variations and modifications may be made to the preferred embodiments of the invention without departing substantially from the spirit and principles of the invention. All such modifications and variations are intended to be included herein within the scope of the present invention, as defined by the following claims.

We claim:

1. A method for high spatial resolution imaging of a structure of interest in a specimen, having the steps:
    selecting a substance from a group of substances,
        which have a first electronic state in which they can be excited by light of one wavelength to spontaneously emit fluorescent light,
        which can be converted from their first electronic state into a second electronic state by the light of the one wavelength,
        which can not be excited by the light of the one wavelength to spontaneously emit fluorescent light in their second electronic state, and
        which can return from their second electronic state into their first electronic state;
    marking the specimen's structure of interest with molecules of the substance;
    imaging the specimen onto a sensor array, a spatial resolution limit of the imaging being greater than an average spacing between closest neighboring molecules of the substance in the specimen;
    exposing the specimen to the light of the one wavelength in at least one region which has dimensions larger than the spatial resolution limit of the imaging of the specimen onto the sensor array at such an intensity that changing fractions of the molecules of the substance being in their first electronic state are, by the light of the one wavelength, excited to spontaneously emit fluorescent light and converted into their second electronic state, and that at least 10% of the molecules of the substance that are respectively in the first electronic state lie at a distance from their closest neighboring molecules in the first state which is greater than the spatial resolution limit of the imaging of the specimen onto the sensor array;
    registering the fluorescent light which is spontaneously emitted by the molecules of the substance in the region, in a plurality of images recorded by the sensor array during continued exposure of the specimen to the light of the one wavelength; and
    determining the position in the specimen of the molecules of the substance that are respectively in the first electronic state, which lie at a distance from their closest neighboring molecules in the first electronic state which is greater than the spatial resolution limit of the imaging of the specimen onto the sensor array, from the images recorded by the sensor array.

2. The method of claim 1, wherein the substance is not switchable.

3. The method of claim 1 wherein the first electronic state is a singlet state and the second electronic state is a triplet state of the substance.

4. The method of claim 1, wherein at the start of the exposure of the specimen to the light of the one wavelength, its intensity is set to be so high that more than 90% of the molecules of the substance are converted into their second electronic state.

5. The method of claim 4, wherein at the start of the exposure of the specimen to the light of the one wavelength, its intensity is set to be so high that essentially all of the molecules of the substance are converted into their second electronic state.

6. The method of claim 1, wherein the substance is selected from a subgroup of substances which includes
    substances which return spontaneously from their second electronic state into their first electronic state;
    substances which return from their second electronic state into their first electronic state by the action of the light of the one wavelength; and
    substances which return into their first electronic state spontaneously and by action of the light of the one wavelength.

7. The method of claim 1, wherein at least one measure is implemented which modifies the lifetime of the second electronic state of the fluorescent dye in the specimen.

8. The method of claim 7, wherein at least one measure is implemented which extends the lifetime of the second electronic state of the fluorescent dye in the specimen.

9. The method of claim 1, wherein, before the images are recorded, a fraction of the substance is converted by photobleaching by means of a high intensity of light, which is selected from the light of the one wavelength and the light of another wavelength, into a persistent dark state which differs from the first electronic state and the second electronic state.

10. The method of claim 1, wherein the intensity of the light of the one wavelength is set to a constant value during the recording of the images.

11. The method of claim 1, wherein the intensity of the light of the one wavelength is set to an intensity profile, time-modulated with the sequence of the recording of the images, during the recording of the images.

12. The method of claim 1, wherein the light of the one wavelength is directed continuously onto the region of the specimen.

13. The method of claim 1, wherein the light of the one wavelength is directed onto the region of the specimen in rapid pulses which are not resolved during the recording of the images.

14. The method of claim 1, wherein the individual recorded images are evaluated online as to whether they show inseparable fluorescent molecules of the substance, and in that the intensity of the light is varied until the density of such inseparable fluorescent molecules falls below a predefined threshold.

15. The method of claim 1, wherein the individual recorded images are evaluated online in respect of the maximum density in which they show separable fluorescent molecules of the substance, and in that the intensity of the light is varied until a density threshold for such separable fluorescent molecules is reached.

16. The method of claim 1, wherein at the start of exposing the specimen to the light of the one wavelength, an intensity distribution of the fluorescent light of the entire substance in the specimen is recorded by the sensor array with the spatial resolution of the imaging of the specimen onto the sensor array.

17. The method of claim 1, wherein a termination criterion for the recording of further images of the same region of the specimen is defined on the basis of the intensity distribution of the fluorescent light of the entire substance in the specimen.

18. The method of claim 1, wherein each position of a molecule of the substance registered in one of the plurality of images is convoluted with the PSF (Point Spread Function) of the imaging of the specimen onto the sensor array or with a function derived therefrom, and in that this reconstruction is compared with the initially recorded intensity distribution.

19. The method of claim 1, wherein the specimen's structure of interest is marked with the substance by modifying a biological specimen with gene technology so that it itself expresses the substance.

20. The method of claim 1, wherein the specimen's structure of interest is marked with the substance by modifying a biological specimen with gene technology so that it expresses proteins with specific binding sites for the substance or a linker coupled to the substance.

* * * * *